US00PP29780P2

(12) United States Plant Patent
Verschoor

(10) Patent No.: US PP29,780 P2
(45) Date of Patent: Oct. 30, 2018

(54) ***VERONICA* PLANT NAMED 'VERSPI'**

(50) Latin Name: *Veronica spicata*
Varietal Denomination: Verspi

(71) Applicant: Janus Verschoor, Haarlem (NL)

(72) Inventor: Janus Verschoor, Haarlem (NL)

(73) Assignee: A. VERSCHOOR HORTICULTURE IMPORT-EXPORT BV, Haarle (NL)

( * ) Notice: Subject to any disclaimer, the term of this patent is extended or adjusted under 35 U.S.C. 154(b) by 0 days.

(21) Appl. No.: 15/731,279

(22) Filed: May 17, 2017

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Susan Beth McCormick Ewoldt
(74) *Attorney, Agent, or Firm* — Penny J. Aguirre

(57) ABSTRACT

A new cultivar of *Veronica* named 'Verspi' that is characterized by its compact and dwarf plant habit, its numerous flowering stems, its re-blooming habit resulting in a long bloom season, and its bright pink flowers.

2 Drawing Sheets

Botanical classification: *Veronica spicata.*
Cultivar designation: 'Verspi'.

BACKGROUND OF THE INVENTION

The present invention relates to a new and distinct cultivar of *Veronica spicata* and will be referred to hereafter by its cultivar name, 'Verspi'. 'Verspi' represents a new herbaceous perennial grown for landscape use.

'Verspi' was selected by the Inventor as a seedling in a seedling bed in Haarlem, The Netherlands in summer of 2010. The seedling bed had been planted with a mixture of *Veronica spicata* seed from unknown parents.

Asexual propagation of the new cultivar was first accomplished by stem cuttings by the Inventor in summer of 2013 in Haarlem, The Netherlands. Asexual propagation by cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Verspi' as a unique cultivar of *Veronica.*

1. 'Verspi' exhibits a compact and dwarf plant habit.
2. 'Verspi' exhibits numerous flowering stems.
3. 'Verspi' exhibits a re-blooming habit resulting in a long bloom season.
4. 'Verspi' exhibits bright pink flowers.

'Verspi' can be most closely be compared to the *Veronica spicata* cultivars (not patented) and 'Glory' (U.S. Plant Pat. No. 18,932). Both are similar to 'Verspi' in having compact plant habits. 'Heidekind' differs from 'Verspi' in having less flowering stems, a shorter bloom period, and in being taller in height (less compact). 'Glory' differs from 'Verspi' in having a shorter bloom period (lacks a re-blooming habit), in being taller in height (less compact), and in having flowers that are violet-blue in color.

BRIEF DESCRIPTION OF THE DRAWINGS

The accompanying colored photographs illustrate the overall appearance and distinct characteristics of the new

*Veronica*. The photographs were taken of nine month-old plants of 'Verspi' as field grown in Haarlem, The Netherlands and place in a 17-cm container for the photographs.

Figure 1:
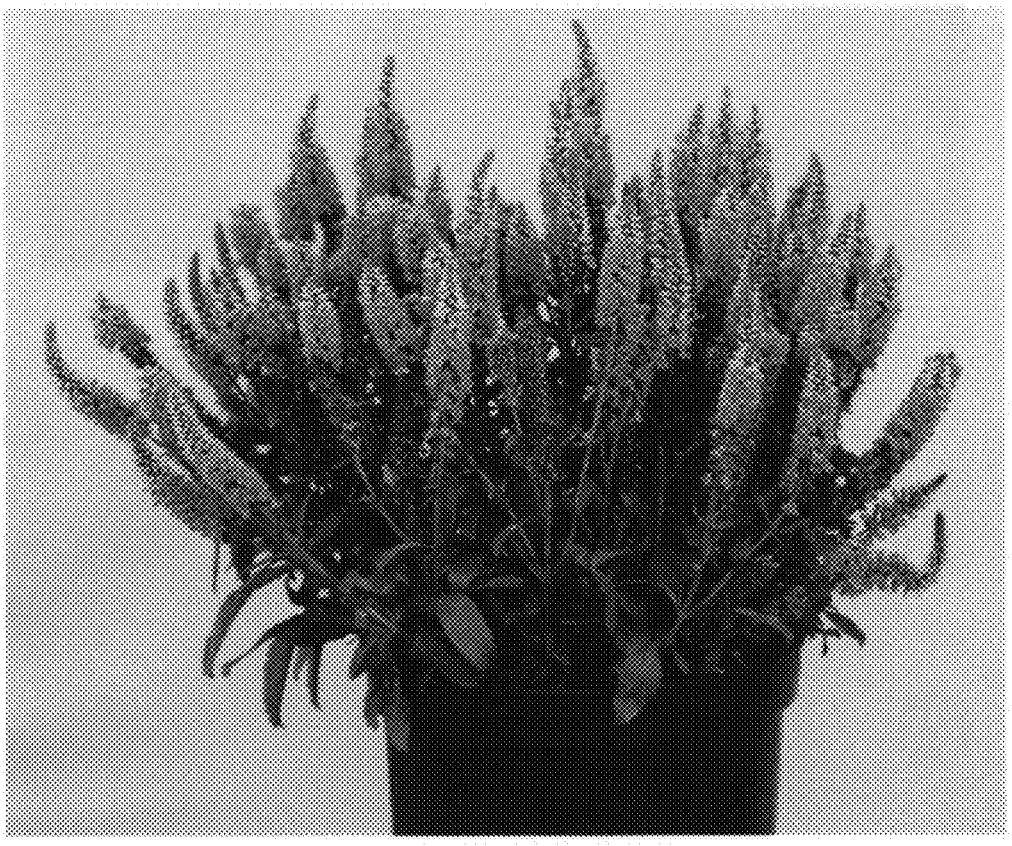

The photograph in FIG. 1 provides a side view of a plant of 'Verspi' in bloom.

Figure 2:
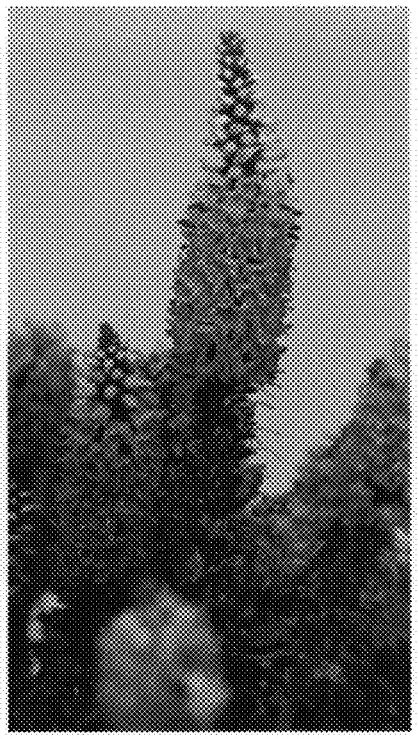

The photograph in FIG. 2 provides a close-up view of the inflorescences of 'Verspi'.

Figure 3:
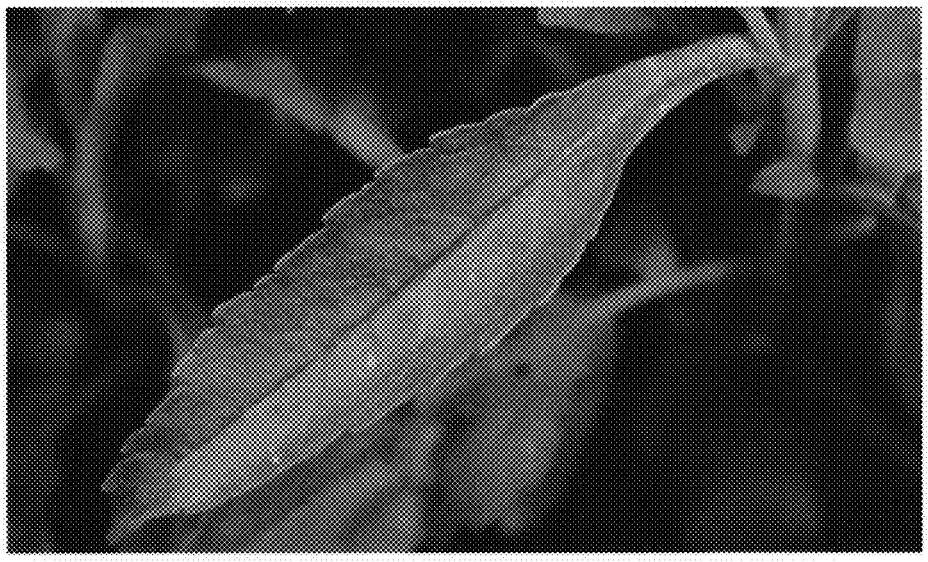

The photograph in FIG. 3 provides a close-up view of a leaf of 'Verspi'.

The colors in the photograph may differ slightly from the color values cited in the detailed botanical description, which accurately describe the colors of the new *Veronica.*

DETAILED BOTANICAL DESCRIPTION

The following is a detailed description of the new cultivar as observed for a plant about 9-months in age as field grown outdoors in Haarlem, The Netherlands. The plants were grown under average day temperatures of 15° to 30° C. and average night temperatures of 10° to 20° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Re-blooming from late spring into autumn in The Netherlands.

*Plant type.*—Herbaceous perennial.

*Plant habit.*—Compact, dwarf.

*Height and spread.*—Reaches about 28 cm in height and 32 cm in spread.

*Hardiness.*—At least in U.S.D.A. Zones 4 to 9.

*Diseases.*—No susceptibility or resistance to diseases has been observed.

*Plant vigor.*—Slow to moderate.

*Propagation.*—Stem cuttings.

*Root development*.—About 1.5 weeks to initiate roots and 3 to 4 weeks to finish in a one-gallon container from rooted cutting.

*Growth rate*.—Low to moderate.

Stem description:

*Shape*.—Round.

*Stem quantity*.—Average of 16 main branches, 6 secondary branches per branch.

*Stem color*.—Young stems; 144A, mature stems and internodes; 143C.

*Stem size*.—Average of 3 mm in diameter and 17.6 cm (excluding inflorescence) in length.

*Stem surface*.—Slightly glossy and densely covered with soft pubescence hairs; an average of 0.2 mm in length and too fine to measure color.

*Stem strength*.—Strong.

*Stem aspect*.—Held at an average angle of 20° to vertical.

*Branching habit*.—Freely branching from the base.

*Internode length*.—Average of 2 cm.

Foliage description:

*Leaf division*.—Simple.

*Leaf arrangement*.—Opposite.

*Leaf shape*.—Narrow ovate to very slightly carinate.

*Leaf size*.—An average of 5.7 cm in length and 1.8 cm in length.

*Leaf number*.—Average of 12 per branch.

*Leaf base*.—Attenuate.

*Leaf apex*.—Acute.

*Leaf margin*.—Crenate-serrate.

*Leaf venation*.—Pinnate, upper surface 144A in color, lower surface 143B in color.

*Leaf surface*.—Upper surface slightly glossy, lower surface matte, both surfaces slightly covered with very short pubescent hairs; too fine to measure color, average length of hairs is 0.2 mm in length.

*Leaf color*.—Young upper surface; 137B, young lower surface; 137C, mature upper surface; between NN137A and 147A, mature lower surface; 137C.

*Petiole*.—Average of 2.1 cm in length, 3 mm in diameter, slightly carinate, both surfaces slightly glossy and slightly pubescent covered with very short hairs an average of 0.2 mm in length and too small to measure color.

Flower description:

*Inflorescence type*.—Compound terminal racemes of rotate-shaped flowers.

*Lastingness of inflorescence*.—Individual flowers last an average of 7 days, self-cleaning, inflorescence lasts about 3 weeks.

*Inflorescence size*.—Average of 6.4 cm in length and 1.9 cm in diameter.

*Flower type*.—Terminal and axillary racemes.

*Flower number*.—Average of 130 per inflorescence, 5,000 per plant.

*Flower aspect*.—Outward facing.

*Flower fragrance*.—None.

*Flower buds*.—Ovate in shape, average of 6 mm in length and 2 mm in diameter, 62A in color, immature calyx 138B in color.

*Flower size*.—About 7 mm in depth and width.

*Flower shape*.—Campanulate.

*Peduncle*.—7.8 cm in length and 2 mm in diameter, held vertically, strong, 143B in color, surface is matte and covered with soft, short pubescence an average of 2 mm in length and too small to measure color.

*Pedicels*.—An average of 0.5 mm in length and width, held at an average angle of 45°, moderately strong, surface is matte and covered with soft, short pubescence an average of 2 mm in length and too small to measure color.

*Calyx*.—Rotate in shape, average of 4 mm in length and 2.5 mm in diameter.

*Sepals*.—4, rotate, 1 whorl, ovate in shape, base is broad cuneate, acute apex, margin, acute apex, lower sepals 4 mm in length and 1 mm in width, upper sepals 3 mm in length and 1 mm in width, color; upper surface when opening and fully open 137C, lower surface when opening and fully open 138B, upper surface matte, upper and lower surface covered with soft, short pubescence 0.2 mm in length and too small to measure color.

*Petals*.—4, 1 whorl, obovate in shape, obtuse apex, lower 35% fused, lobes; entire margin, both surfaces glabrous and matte, average of 7 mm in length and 3.5 mm in width, color when opening upper and lower surface 67C, color when fully open upper and lower surface 68D, color upper and lower surfaces when fading 68D, tube; 2.5 mm in length, 1.5 mm in diameter, outer surface is glabrous, inner surface densely covered with soft hairs; 0.75 mm in length and NN155D in color, color of tube outer surface 73D, color of tube inner surface (throat) 68B.

Reproductive organs:

*Gynoecium*.—Pistil; 1, 5.5 mm in length, style; 5 mm in length, 70D in color, stigma; club-shaped, N81A in color, ovary; 144C in color.

*Androecium*.—Stamens; 2, filament; 5 mm in length, 68B in color, anthers; double kidney shaped, 1 mm in length, 0.75 mm in width, color between N186A and N186C in color, pollen; moderate in quantity, 4C in color.

*Fruit*.—Fruit and seed production has not been observed to date.

It is claimed:

1. A new and distinct cultivar of *Veronica* plant named 'Verspi' as herein illustrated and described.

* * * * *